United States Patent [19]

Sakai

[11] 4,028,186

[45] June 7, 1977

[54] PROCESS FOR THE PRODUCTION OF SACCHARIFIED STARCH PRODUCTS

[75] Inventor: Shuzo Sakai, Okayama, Japan

[73] Assignee: Kabushiki Kaisha Hayashibara Seibutsu Kagaku Kenkyujo, Okayama, Japan

[22] Filed: July 10, 1975

[21] Appl. No.: 594,679

[30] Foreign Application Priority Data

Nov. 30, 1974 Japan .................... 49-137174

[52] U.S. Cl. .................. 195/31 R; 195/62
[51] Int. Cl.$^2$ ......................... C12D 13/02
[58] Field of Search ........... 195/11, 7, 31 R, 66 R, 195/62, 65, 13, 64

[56] References Cited

UNITED STATES PATENTS

| | | | |
|---|---|---|---|
| 3,677,896 | 7/1972 | Kurimoto et al. | 195/31 R |
| 3,795,584 | 3/1974 | Mitsuhashi et al. | 195/31 R |

OTHER PUBLICATIONS

Bird et al., "The Action of some α-Amylases on Amylose", *Biochemical Journal*, vol. 56, pp. 86–99 (1954).
Piendl, "Enzymic Behavior of Bottom Flocculating and Nonflocculating Yeast during Fermentation", *Chemical Abstracts*, vol. 76, No. 19, p. 363, Abs. No. 1116516 (1972).
Nitta et al., "Influence of Molecular Structure of Substrates and Analogues on Taka-Amylase A Catalyzed Hydrolases," *J. Biochem.*, vol. 69, No. 3, pp. 577–588 (1971).
*Starch Handbook*, p. 694.

*Primary Examiner*—Raymond N. Jones
*Assistant Examiner*—Thomas G. Wiseman
*Attorney, Agent, or Firm*—Browdy and Neimark

[57] ABSTRACT

A process for the production of saccharified starch products, which is characterized by subjecting a starch hydrolysate with a high maltose purity to the action of an alpha-amylase with a maltotriose-decomposing activity versus dextrinogenic activity ratio of 0.001 – 0.1.

1 Claim, No Drawings

PROCESS FOR THE PRODUCTION OF SACCHARIFIED STARCH PRODUCTS

FIELD OF THE INVENTION

The present invention relates to a process for the production of saccharified starch products wherein maltose is the predominant constituent, which is characterized by increasing the maltose purity of the products while lowering their maltotriose content by allowing an alpha-amylase with a maltotriose-decomposing activity versus dextrinogenic activity ratio in the range of 0.001–0.1 to act on a saccharified starch hydrolysate during its saccharification with the use of a maltogenic enzyme or after such saccharification. The terms "maltotriose-decomposing activity" and "dextrinogenic activity" will be used throughout the specification as clarified later in the specification. Hereinafter, all parts and percents will be given by weight, dry solid basis (d.s.b.), unless specified otherwise.

BACKGROUND OF THE INVENTION

The recent successive findings of the many advantageous features of maltose have led to the rapid expansion of uses for maltose. Thus, saccharified starch products, wherein maltose is the predominant constituent, are drawing much attention and receiving ever-increasing demand from many fields, especially from the food processing and pharmaceutical industries.

Conventionally, saccharified starch hydrolysates with a maltose purity in the range of 40–50% were obtained by subjecting liquefied starch to the action of a maltogenic enzyme, malt amylase. More recently, with the employment of starch-debranching enzyme and beta-amylase, saccharified starch hydrolysates with maltose purity of 50% or higher have become obtainable with considerable ease.

Maltotriose, necessarily, forms abundantly in saccharified starch hydrolysates which are prepared from starch with maltogenic enzyme(s), for example beta-amylase and starch-debranching enzyme, and wherein maltose is the predominant constituent. Since the formed maltotriose is not decomposable by such eenzymes, the increment of maltose purity was so far restricted. Thus the inventors found that decomposition or conversion of the maltotriose present in said hydrolysates into maltose is required to improve further the maltose purity.

SUMMARY OF THE INVENTION

The present invention is based on alpha-amylase which received practically no attention as a maltotriose-decomposing activity enzyme (hereinafter referred to as maltotriase) and on its feasibility to decompose the maltotriose content of the saccharified starch hydrolysates with the objective to obtain saccharified starch products with higher maltose purity.

The fact that alpha-amylase is relatively stable against high temperature is well known. Also well known are that, in general, alpha-amylase acts on higher molecular substrates with ease but a difficulty is rendered when it acts on lower molecular substrates such as maltotriose, and that enzyme has a disadvantage of being susceptive to competitive inhibition which is effected by maltose.

The inventors concentrated their efforts to the research on alpha-amylase which possess a maltotriase activity and to the development of a process feasible for obtaining saccharified starch products with higher maltose purity by the decomposition of the maltotriose content in saccharified starch hydrolysates.

As a result, the inventors found the astonishing fact that the higher the maltose purity of the substrate, i.e., saccharified-starch hydrolysate, the more the alpha-amylase with a maltotriase activity versus dextrinogenic activity ratio (hereinafter referred to as m/d ratio) in the range of 0.001 to 0.1 would effect decomposition of the maltotriose present in the hydrolysates to improve further their maltose purity. Alpha-amylases with an m/d ratio in said range are produced by fungi of genera Aspergillus, Rhizopus, Peenicillium and Oospora.

DESCRIPTION OF PREFERRED EMBODIMENTS

Any starch is employable in the invention regardless of its origin, for example those derived from cereals, grains, seeds, tubers and roots, and of its amylose to amylopectin proportion. In order to obtain a saccharified starch hydrolysate solution with a high maltose purity, starch slurry is at first gelatinized or liquefied. Then saccharification of the gelatinized or liquefied starch is effected with beta-amylase or a combination of beta-amylase and starch-debranching enzyme.

In general, enzymatic preparations such as those derived from wheat bran (cf. Specification of Japanese Patent Publication No. 70-18937), soybean and sweet potato may be used as beta-amylase. As for starch-debranching enzymes, pullulanase and isoamylase prepared from a culture broth of a microorganism selected from a group of genera *Escherichia intermedia* ATCC 21073, *Aerobacter aerogenes* ATCC 8724, *Pseudomonas amyloderamosa* ATCC 21262, *Corynebacterium sepedonicum* IFO 3306, *Aeromonas hydrophyla* IFO 3820, *Flavobacterium esteroaromaticum* IFO 3751, *Vibrio metachnikovii* IFO 1039, *Actinoplanes philippinensis* ATCC 12427, *Streptosporangium roseum* ATCC 12428, as described in Japanese Patent Publication No. 68-28939, Japanese Patent Publication No. 69-8070, Japanese Patent Publication No. 70-9229, Japanese Patent Publication No. 70-16788, Japanese Patent Publication No. 71-28151 and Japanese Patent Publication No. 73-18826, are employable.

The saccharification provides saccharified starch hydrolysates wherein the maltotriose content is, generally, about 5–25%, dependent on the reaction method used, and the maltose purity is limited to about 50–93%.

The higher the maltose purity of the saccharified starch hydrolysate, the more desirable the hydrolysates would be as a substrate for the alpha-amylase of the present invention with an m/d ratio of 0.001–0.1. Particularly, starch hydrolysates with a maltose purity of 80% or higher is preferable, as well as a hydrolysate with a concentration ranging from 2.0 to 30.0% which gives favorable results. As to reaction conditions, a temperature of 30°–70° C, a pH value of 3.0–9.0, an addition of alpha-amylase in the amount of one or more units of dextrinogenic activity per gram saccharified starch hydrolysate saccharified, d.s.b., are preferable, and the addition of alpha-amylase may be either during the saccharification of the starch hydrolysate or thereafter. More particularly, the alpha-amylase may be allowed to act on the saccharified starch hydrolysate together with a maltogenic enzyme(s) or after saccharification of the saccharified starch hydrolysate with a maltogenic enzyme(s).

Throughout the specification, maltogenic enzyme means an enzyme which effects, formation of maltose from starch but not a decline in maltose purity.

With the utilization of the action of the alpha-amylase possessing the specified range of m/d ratio, the maltotriose content, which is present in the saccharified starch hydrolysate(s) and inhibits further improvement in maltose purity, is decomposed and the maltose purity of the final products is improved remarkably.

The resulting saccharified starch products are then heated to inactivate the enzyme(s), filtered, decolorized with activated carbon and subjected to deionization with ion exchangers.

Syrup, crystalline and powder products are obtained in yields of 96–99% based on material starch hydrolysate after concentration.

The methods for enzymatic activity assay and quantitative assay of sugar composition were as follows.

Dextrinogenic activity assay

A mixture consisting of 5 ml of a 1 w/v% soluble-starch solution and 4 ml of a 0.1M acetate buffer solution, pH 5.3, was preheated to 40° C in a test tube, one ml of an enztmatic solution was added with appropriate stirring, and subjected to reaction at 40° C. At intervals, 0.5 ml samples were withdrawn, which were stained by additions to 0.5 ml portions of a 0.002N $I_2$—KI solution prepared beforehand in smaller test tubes. The reaction time for a certain sample to attain the color equivalent to the standard color of a 0.1N $I_2$—KI solution was determined. One unit of dextrinogenic activity was expressed as the potency that effects exhibition of the equivalent color after ten-minute reaction.

Maltotriase activity (Maltotriose-decomposing activity) assay

To 10 ml of a 0.1M acetate buffer, pH 6.0, containing 0.55 w/v% maltotriose was added 0.5 ml of an exzymatic solution and incubated at 40° C. The glucose formation per ml reaction mixture was assayed in accordance with the glucose-oxidase method (J. B. Lloyd and W. J. Whelan: "Anal. Biochem.", Vol. 30, 467, 1969) and the amount of enzyme which effected hydrolysis of one $\mu$mole of maltotriose at 40° C over a period of 1 minute was designated as one unit of maltotriase.

Maltase (Maltose-decomposing) activity

Quantitative assay and calculation were carried out similarly as maltotriase activity except that maltotriose was replaced with maltose.

Quantitative assay of sugar composition

Developed paper chromatograms obtained in accordance with the method described in "Sugar Handbook", 686–687; editors, Hamaguchi and Sakurai; publisher, Asakura Shoten Inc., Tokyo, Japan (1964), were fractionated into each composition which was determined quantitatively be the anthrone method and expressed in percentage.

The preparation of alpha-amylases with the m/d ratio of 0.001–0.1 will be illustrated. Cultivation of a microorganism that produces the alpha-amylase is carried out, usually, by inoculating a strain of the microorganism on a liquid or solid culture medium, containing carbon-, nitrogen- and inorganic-sources and traces of growth factors and which is sterilized by heating at a temperature of 120° C for 10–40 minutes, and incubating the mixture at 20°–35° C under stationary conditions or with agitation by aeration for 1–7 days.

The alpha-amylase-containing solution prepared from the culture medium is purified by filtration or centrifugation. Especially, in case the alpha-amylase is endocellularly produced in mycelium, the amylase may be extracted from the mycelium by known methods, for example treatment with either ultrasonics, freezing and thawing, autolysis, cell-wall-decomposing enzyme, surface active agent or a combination thereof. The thus obtained alpha-amylase may be used intact if its m/d ratio is in the range of 0.001–0.1. In case an alpha-amylase of higher purity is desirable, the enzyme may be purified by any fractionation method such as thermal treatment, pH treatment, salting-out and gel filtration.

In case the activity of the alpha-amylase is excessively low, the enzyme may be concentrated by such procedures as precipitation with ammonium sulfate or organic solvent, and vacuum evaporation. A commercially available alpha-amylase with an m/d ratio in the specified range may be used intact or after purification if necessary.

Even impure alpha-amylase, for example those wherein glucoamylase or alpha-glucosidase co-exists, may be used intact provided that they have an m/d ratio in the range of 0.001–0.1 and that the improvement of maltose purity is not substantially inhibited. In this case, an employment of an alpha- amylase with a maltotriase activity versus maltase activity ratio of 2.5 or higher is preferable.

Even if the alpha-amylase is contaminated with enzymes that hinder improvement in maltose purity, the efficacy of the amylase can be still sufficiently exhibited in the co-existence of inhibitor of the enzymes that prevent maltose purity improvement.

The invention will be illustrated further with reference to the following experiments.

EXPERIMENT 1

As substrate a commercialized starch hydrolysate with a high maltose purity was used at a concentration of 0.2–40%. The results obtained by saccharifying the hydrolysate with the addition of alpha-amylase in the amount of 50 dextrinogenic-activity units per gram solid at pH 6.0 and 40° C for 20 hours are listed in Table 1.

Alpha-amylase was prepared as follows. To 15 parts of an aqueous solution comprising 0.1w/v% $NH_4NO_3$, 0.1w/v% $NaNO_3$, 0.2w/v% polypeptone, 0.1w/v% $K_2HPO_4$, 0.05w/v% $MgSO_4$ $7H_2O$ and 0.05w/v% KCl was added 10 parts of wheat bran with thorough mixing, and the resulting mixture was autoclaved at 120° C for 30 minutes, then used as culture medium. To each portion of the medium was inoculated individually a member of the fungal group comprising *Aspergillus oryzae* IFO 5710, *Aspergillus niger* IAM 2534, *Penicillus crysogenum* IAM 7326, *Rhizous japonicus* IFO 4758 and *Oospora aurantia* IFO 4606 and the inoculated media were incubated at 27° C for 5 days. Then the cultures were subjected to extraction at 35° C for 2 hours after adding 100 parts of water. To each of the filtrates obtained by filtrating the extracts was then added two-fold volumes of cold acetone to effect precipitation. The precipitates that eluted in water were dialized. The dialized solutions were then applied twice to columns of DEAE-cellulose with a gradient of 0.02–0.5M NaCl, and the alpha-amylase zones were collected and used after salting-out with ammonium sulfate.

Malt alpha-amylase was prepared by the method described by S. Schwimmer and A. K. Balls in J. Biol. Che., vol. 179, 1063, (1949).

The bacterial liquefying alpha-amylase, bacterial saccharogenic alpha-amylase and Taka-amylase A used in the Experiments and Examples were crystalline products purchased from Seikagaku Kogyo Co., Ltd., Tokyo, Japan.

increases in maltose purity in the resulting saccharified starch product obtained by allowing such enzyme to act on material starch hydrolysate.

Comparison tests using an alpha-amylase with an m/d ratio in the range of 0.001–0.1 showed that material starch hydrolysates possessing respective concentrations of 0.2 and 40% showed only a slight effect on improving the resulting maltose purity. Another finding was that when the concentration of the material starch hydrolysate is in the range of 2.0–30.0% the maltotri- Table I.

| Alpha-amylase source | Maltotriase activity / Dextrinogenic activity | Starch hydrolysate concentration, % | Sugar composition, % | | | | Efficacy |
|---|---|---|---|---|---|---|---|
| | | | $G_1$ | $G_2$ | $G_3$ | Dext | |
| Control-no d-amylase | | | 0.4 | 90.5 | 7.4 | 1.7 | |
| Taka-amylase A, crystal | 0.0311 | 0.2 | 0.8 | 91.7 | 5.8 | 1.7 | ± |
| | | 2.0 | 2.0 | 93.5 | 3.2 | 1.3 | + |
| | | 5.0 | 2.8 | 94.6 | 1.0 | 1.6 | + |
| | | 10.0* | 2.9 | 93.8 | 1.8 | 1.5 | + |
| | | 10.0 | 3.4 | 94.8 | 0.7 | 1.1 | + |
| | | 15.0 | 3.7 | 94.0 | 0.9 | 1.4 | + |
| | | 20.0 | 4.2 | 93.2 | 1.2 | 1.4 | + |
| | | 25.0 | 4.4 | 93.0 | 1.3 | 1.3 | + |
| | | 30.0 | 4.7 | 92.3 | 1.4 | + | |
| | | 40.0 | 5.3 | 90.8 | 2.2 | 1.7 | ± |
| Aspergillus oryzae IFO 5710 | 0.0062 | 0.2 | 1.0 | 91.6 | 5.8 | 1.6 | ± |
| | | 2.0 | 2.7 | 93.0 | 2.9 | 1.4 | + |
| | | 10.0 | 3.0 | 94.1 | 1.3 | 1.6 | + |
| | | 20.0 | 3.9 | 93.5 | 1.0 | 1.6 | + |
| | | 30.0 | 4.8 | 92.3 | 1.3 | 1.6 | + |
| | | 40.0 | 5.8 | 90.3 | 2.2 | 1.7 | ± |
| Aspergillus niger IAM 2534 | 0.0145 | 0.2 | 0.8 | 91.7 | 5.8 | 1.7 | ± |
| | | 2.0 | 2.0 | 93.5 | 3.1 | 1.4 | + |
| | | 10.0 | 2.6 | 94.4 | 1.8 | 1.2 | + |
| | | 20.0 | 3.0 | 93.0 | 2.6 | 1.4 | + |
| | | 30.0 | 3.0 | 92.2 | 3.4 | 1.4 | + |
| | | 40.0 | 3.5 | 91.2 | 3.7 | 1.6 | ± |
| Penicillium crysogenum IAM 7326 | 0.0139 | 0.2 | 1.2 | 91.3 | 6.0 | 1.5 | ± |
| | | 10.0 | 3.2 | 94.8 | 0.9 | 1.1 | + |
| | | 20.0 | 3.8 | 93.3 | 1.3 | 1.6 | + |
| Rhizopus japonicus IFO 4758 | 0.0048 | 5 | 3.4 | 93.0 | 1.9 | 1.7 | + |
| | | 10 | 3.6 | 94.5 | 0.8 | 1.1 | + |
| | | 20 | 4.8 | 93.3 | 0.6 | 1.3 | + |
| Oospora aurantia IFO 4606 | 0.0157 | 5 | 2.1 | 94.4 | 2.1 | 1.4 | + |
| | | 10 | 3. | 93.9 | 1.4 | 1.5 | + |
| | | 20 | 3.5 | 93.8 | 1.5 | 1.2 | + |
| Bacterial liquefying alpha-amylase, crystal | Less than 0.0001 | 0.2 | 0.4 | 90.3 | 7.6 | 1.7 | ± |
| | | 2.0 | 0.5 | 90.8 | 6.7 | 2.0 | ± |
| | | 10.0 | 0.9 | 90.9 | 6.8 | 1.4 | ± |
| | | 20.0 | 0.7 | 90.7 | 6.6 | 2.0 | ± |
| | | 30.0 | 0.8 | 89.9 | 1.9 | ± | |
| | | 40.0 | 0.4 | 90.7 | 6.8 | 2.1 | ± |
| Bacterial saccharogenic alpha-amylase, crystal | 0.5580 | 0.2 | 73.7 | 23.5 | 1.3 | 1.5 | − |
| | | 2.0 | 77.0 | 20.1 | 1.0 | 1.9 | − |
| | | 10.0 | 68.6 | 28.7 | 0.8 | 1.9 | − |
| | | 20.0 | 64.4 | 31.7 | 1.5 | 2.4 | − |
| | | 30.0 | 64.5 | 29.6 | 2.3 | 3.6 | − |
| | | 40.0 | 60.3 | 32.0 | 3.0 | 4.7 | − |
| Malt alpha-amylase | 0.00047 | 5.0 | 0.9 | 90.6 | 6.8 | 1.7 | ± |
| | | 10.0 | 1.2 | 90.7 | 6.7 | 1.4 | ± |
| | | 20.0 | 1.4 | 90.6 | 6.3 | 1.7 | ± |

*The amount of enzyme used was 10 units per gram starch hydrolysate solid.
Note: In the Table and throughout the Specification, $G_1$ represent glucose; $G_2$, maltose; $G_3$, maltotriose; dext., dextrins with molecular weights equivalent to or higher than that of maltotetraose; +, results determined as being effective; ±, results that were difficultly determinable by sugar composition as whether effective or not; and −, results determined as being unfavorable.

As apparent from the table, the employment of the bacterial liquefying alpha-amylase with an m/d ratio of lower than 0.001, bacterial saccharogenic alpha-amylase with an m/d ratio of 0.5580 or malt alpha-amylase with the ratio of 0.00047 resulted in no increase in maltose purity over that of the material starch hydrolysate. Particularly, the employment of bacterial saccharogenic alpha-amylase gave a significant decrease in maltose purity.

In contrast to the alpha-amylases, commercialized Takaamylase A (m/d ratio, 0.0311) and those with an m/d ratio of higher than 0.001 but lower than 0.1 and the alpha-amylases derived from Aspergillus oryzae (m/d ratio, 0.0062), Aspergillus niger (0.0145), Penicillium crysogenum ( 0.0139), Rhizopus japonicus (0.0048) or Oospora aurantia (0.0157) gave significant ose is majorly decomposed leading to a significant maltose purity improvement.

EXPERIMENT 2

The Taka-amylase A used in Experiment 1 was added in respective amounts of 50 dextrinogenic-activity units of the enzyme per gram starch hydrolysate solid to 10% aqueous solutions of starch hydrolysates with different sugar compositions and then the mixtures were subjected to reaction at pH 6.0 and 45° C for 24 hours to investigate the effects of the enzyme. The results were as shown in Table II.

Table II.

| Without a-amylase addition | | | | with a-amylase addition | | | | Maltose formation, %* |
|---|---|---|---|---|---|---|---|---|
| $G_1$ | $G_2$ | $G_3$ | Dext | $G_1$ | $G_2$ | $G_3$ | Dext | |
| 7.6 | 43.0 | 14.3 | 35.1 | 9.3 | 45.7 | 12.6 | 32.4 | 18.9 |
| 2.8 | 52.0 | 14.0 | 31.2 | 6.7 | 55.1 | 11.5 | 26.7 | 22.1 |
| 1.5 | 74.0 | 13.5 | 11.0 | 4.5 | 77.0 | 9.5 | 9.0 | 22.2 |
| 1.3 | 81.8 | 8.1 | 8.8 | 3.2 | 85.1 | 4.3 | 7.4 | 40.7 |
| 0.9 | 87.9 | 7.5 | 3.7 | 3.4 | 91.6 | 1.9 | 3.1 | 49.3 |
| 0.4 | 92.5 | 5.1 | 2.0 | 2.3 | 95.5 | 1.1 | 1.1 | 58.8 |
| 0.4 | 94.5 | 4.1 | 1.0 | 1.6 | 96.7 | 0.8 | 0.9 | 53.7 |

Note:
*Maltose formation, % =

$$\frac{(G_2 \text{ formation following reaction}) \text{ minus } (G_2 \text{ content prior reaction})}{G_3 \text{ content prior reaction}} \times 100$$

As apparent from the results given in the Table, it was found that the higher the maltose purity in the material starch hydrolysate, the more the Taka-amylase effects decomposition of the maltotriose therein to improve further the maltose purity. Especially, the employment of a substrate with a sugar composition in which the maltose content exceeds 80% results in a higher conversion of maltotriose into maltose. The finding was entirely unpredictable from prior knowledge wherein it was believed that the action of alpha-amylase is susceptive to competitive inhibition by maltose. The present invention will be illustrated in more detail with reference to the following Examples which are some preferred embodiments of the invention but not understood as restricting its scope.

EXAMPLE I.

One part of potato starch was admixed to 10 parts of water containing one unit of bacterial liquefying alpha-amylase per gram starch with agitation and the mixture was adjusted to a pH of 6.0. This suspension was then heated to 90° C to effect concurrent gelatinization and liquefaction, then heated immediately up to a temperature of 130° C where it was kept for 5 minutes. Thereafter the resultant was cooled quickly to 50° C, and, after adding respective 20 units of a starch-debranching enzyme prepared from a culture broth of *Escherichia intermedia* ATCC 21073 and a soybean beta-amylase (Product No. 1500 of Nagase & Co., Ltd., Osaka, Japan) per gram starch thereto, the mixture was subjected to saccharification at a temperature of 50° C over 46 hours while maintaining the pH at 6.0. The resultant was designated as hydrolysate A.

The hydrolysate collected at 24 hours after commencing the saccharification and the inactivated 46-hours saccharified hydrolysate were designated respectively as hydrolysates "B" and "C." Hydrolysates B and C were subjected to further saccharification for additional 22 hours after adding thereto respective 100 dextrinogenic-activity units of a Taka-amylase A product commercialized by the above mentioned Seikagaku Kogyo Co., Ltd., which was prepared from *Aspergillus oryzae* and with an m/d ratio of 0.0311, and the resulting products were designated b and c. The results were as listed in Table III.

Table III.

| | Sugar composition, % | | | |
|---|---|---|---|---|
| | $G_1$ | $G_2$ | $G_3$ | Dext |
| (A) | 0.6 | 91.5 | 5.2 | 2.7 |
| (b) | 2.7 | 96.0 | 0.3 | 1.0 |
| (c) | 2.7 | 95.1 | 0.5 | 1.7 |

The sugar composition of the starch hydrolysate obtained after the 24 hours saccharification step was 0.2% glucose, 90.3% maltose, 4.9% maltotriose and 4.6% dextrins.

The resulting saccharified starch products A, b and c, were heated to inactivate the enzymes, decolorized with activated carbon, deionized with ion exchangers and then concentrated under reduced pressure. Respective yields of the products were 97% based on material starch solid. Thereafter the products were crystallized and compared as to crystalline shape, size and appearance, times required for centrifugation from mother liquor (hereinafter referred to as "centrifugalling time") and on yield (total yield of first and second crystals), which gave the results as listed in Table IV.

Table IV.

| | Crystalline shape, size and appearance | Centrifugalling time | Yield of crystalline maltose, % |
|---|---|---|---|
| (A) | Good | 100 | 35.0 |
| (b) | Excellent | 37 | 71.4 |
| (c) | " | 42 | 67.7 |

As apparent from the results, the significant efficacy of the Taka-amylase with an m/d ratio of 0.0311 was fully displayed in increasing considerably the maltose purity of the resulting saccharified starch products, whether the alpha-amylase was added so that it would act concurrently in the saccharification step or after completion of the sacharification. Additionally, as shown in the table, the employment of Taka-amylase A reduces the centrifugalling time to about one-half to one-third and approximately doubles the yield of crystalline maltose product, as well as raising the maltose purity significantly. In view of saccharification-time reduction, preferably, the alpha-amylase should be allowed to act concurrently with other enzyme(s).

EXAMPLE II.

To portions of the starch hydrolysate of Example I obtained after the 24 hours saccharification (i.e., hydrolysate B) were added individually respective 50 dextrinogenic-activity units of each alpha-amylase prepared in Experiment 1 per gram starch hydrolysate and subjected to further saccharification similarly as in Example I. The sugar compositions of the thus obtained products were as listed in the following table.

Table V.

| Alpha-amylase source | Maltotriase activity Dextrinogenic activity | Sugar composition, % | | | |
|---|---|---|---|---|---|
| | | $G_1$ | $G_2$ | $G_3$ | Dext |
| Control (no a-amylase) | | 0.6 | 91.5 | 5.2 | 2.7 |
| Taka-amylase A (crystal) *Aspergillus oryzae* | 0.0311 | 2.4 | 95.3 | 0.8 | 1.5 |
| IFO d5710 *Aspergillus niger* | 0.0062 | 2.4 | 95.0 | 0.9 | 1.7 |
| IAM 2534 | 0.0145 | 3.6 | 93.9 | 0.8 | 1.7 |

Table V.-continued

| Alpha-amylase source | Maltotriase activity / Dextrinogenic activity | Sugar composition, % | | | |
|---|---|---|---|---|---|
| | | $G_1$ | $G_2$ | $G_3$ | Dext |
| Penicillium crysogenum IAM 7326 | 0.0139 | 3.4 | 93.9 | 0.9 | 1.8 |
| Rhizopus japonicus IFO 4758 | 0.0048 | 5.0 | 92.9 | 0.7 | 1.4 |
| Oospora aurantia IFO 4606 | 0.0157 | 2.6 | 94.5 | 1.1 | 1.8 |

The concentrates obtained by carrying our purification and concentration similarly as in Example I each had a yield of about 97% based on material starch. The concentrates were then crystallized and investigated on crystalline shape, size, appearance and compared on maltose yield (total of first and second crystals) and yields. The results are listed in Table VI.

The results revealed again the efficacy of the employment of the alpha-amylase with an m/d ratio of 0.001–0.1 in that a significant improvement in maltose purity, reduction in centrifugalling time and an approximately double increase in maltose yield are realized. The thus obtained crystalline maltose is suitable for injection.

EXAMPLE III

To one part of corn starch was added four parts of water containing two units of bacterial liquefying alpha-amylase per gram starch, and the suspension was adjusted to a pH of 6.0. The suspension was then heated to 90° C to effect concurrent gelatinization and liquefaction, and the resultant was maintained at a temperature of 120° C for 10 minutes. Following cooling to 50° C the resultant was added respectively ten units of an isoamylase prepared from *Pseudomonas amyloderamosa* ATCC 21262 and ten units of beta-amylase derived from wheat bran per gram starch solid and subjected to saccharification at 50° C for 46 hours while maintaining the pH at 5.0, whereupon the reaction was suspended by heating the resulting starch hydrolysate to 70° C.

The sugar composition of the product obtained by saccharification of they hydrolysate at a temperature of 50° C, pH 6.0 for 24 hours using the same Taka-amylase A used in Experiment 1 was as listed in Table VII.

Table VII.

| Taka-amylase A addition | $G_1$ | $G_2$ | $G_3$ | Dext |
|---|---|---|---|---|
| No | 1.3 | 81.8 | 8.1 | 8.8 |
| Yes | 3.3 | 85.2 | 4.2 | 7.3 |

The Taka-amylase A-treated saccharified starch products were purified similarly as in Example I and then concentrated to give a moisture content of about 10%. Solidification and grating of the product obtained after seeding rendered much easiness, and the resulting grated product had a yield of about 96% based on material starch.

EXAMPLE IV

A portion of the Taka-amylase A-treated saccharified starch products were purified similarly as in Example III, then concentrated to give a moisture content of about 25%, maltose seeds were added to effect crystallization, and prepared into a massecuite which was spary-dried. The crystalline powder product was obtained in a yield of about 97% based on material starch. In comparison with the hydrolysate prepared without the Taka-amylase A treatment, the thus obtained product was far more desirable as crystalline powder products and possessed considerably improved commercial values in many respects.

What is claimed is:

1. A process for the production of saccharified starch products with a higher maltose purity percent maltose, d.s.b.), comprising subjecting a starch hydrolysate with an 80% or more maltose purity to the action of a fungal alpha-amylase with a maltotriose-decomposing activity versus dextrinogenic activity ratio of 0.001–0.1 wherein the hydrolysate has a concentration of 2.0–30.0% and said step of subjecting to the action of a fungal alpha-amylase is at a temperature of 30°–70° C and a pH of 3.0–9.0.

Table VI.

| Alpha-amylase source | Maltotriase activity / Dextrinogenic activity | Crystalline shape, size and appearance | Centrifugalling time | Yield of crystalline maltose, % |
|---|---|---|---|---|
| Control-no a-amylase | | Good | 100 | 35.0 |
| Taka-amylase A (crystal) | 0.0311 | Excellent | 37 | 70.6 |
| Aspergillus oryzae IFO 5710 | 0.0062 | " | 40 | 71.3 |
| Aspergillus niger IAM 2534 | 0.0145 | " | 42 | 66.3 |
| Penicillium crysogenum IAM 7326 | 0.0139 | " | 40 | 69.5 |
| Rhizopus japonicus IFO 4758 | 0.0048 | " | 43 | 64.8 |
| Oospora aurantia IFO 4606 | 0.0157 | " | 39 | 68.0 |

* * * * *